(12) United States Patent
Li et al.

(10) Patent No.: US 10,006,845 B2
(45) Date of Patent: Jun. 26, 2018

(54) DEVICE FOR EVALUATING FOAMING PROPERTY OF GAS-SOLUBLE SURFACTANT AND APPLICATION THEREOF

(71) Applicant: CHINA UNIVERSITY OF PETROLEUM, Qingdao (CN)

(72) Inventors: Zhaomin Li, Qingdao (CN); Chao Zhang, Qingdao (CN); Binfei Li, Qingdao (CN); Songyan Li, Qingdao (CN); Jiquan Liu, Qingdao (CN); Quanwei Dong, Qingdao (CN)

(73) Assignee: CHINA UNIVERSITY OF PETROLEUM, Qingdao (CN)

(*) Notice: Subject to any disclaimer, the term of this patent is extended or adjusted under 35 U.S.C. 154(b) by 17 days.

(21) Appl. No.: 14/917,857

(22) PCT Filed: May 7, 2015

(86) PCT No.: PCT/CN2015/078483
§ 371 (c)(1),
(2) Date: Dec. 9, 2016

(87) PCT Pub. No.: WO2015/176610
PCT Pub. Date: Nov. 26, 2015

(65) Prior Publication Data
US 2017/0082528 A1 Mar. 23, 2017

(30) Foreign Application Priority Data

May 19, 2014 (CN) .......................... 2014 1 0212430

(51) Int. Cl.
*G01N 3/00* (2006.01)
*G01N 13/00* (2006.01)
(Continued)

(52) U.S. Cl.
CPC ............... *G01N 13/00* (2013.01); *C09K 8/94* (2013.01); *G01F 13/00* (2013.01)

(58) Field of Classification Search
CPC ...... G01N 15/04; G01N 33/343; G01N 11/14; G01N 33/32; G01N 33/2823; G01N 33/18; G01N 1/28; G01N 1/02; G01N 33/442; G01N 13/02; G01N 21/25; G01N 2013/025; G01N 21/78; G01N 7/16; G01N 33/0006; G01N 25/56; G01N 2013/0275;
(Continued)

(56) References Cited

U.S. PATENT DOCUMENTS

4,084,426 A * 4/1978 Gales ................... G01N 33/146
250/577
4,589,276 A 5/1986 Djabbarah
(Continued)

*Primary Examiner* — Lisa Captuo
*Assistant Examiner* — Brandi Hopkins
(74) *Attorney, Agent, or Firm* — CMB Patent Consulting, LLC (57) ABSTRACT

A device for evaluating the foaming property of a gas-soluble surfactant, which comprises a gas source part, an evaluating kettle, a liquid part, and an intermediate container part. The rotation of the evaluating kettle, the gas-soluble surfactant and the supercritical carbon dioxide can be sufficiently and evenly mixed with each other when the solubility of the gas-soluble surfactant in the supercritical carbon dioxide is measured.

6 Claims, 2 Drawing Sheets

(51) Int. Cl.
*G01F 13/00* (2006.01)
*C09K 8/94* (2006.01)

(58) Field of Classification Search
CPC ..... G01N 27/06; Y10T 436/25; G01F 23/241; G01F 23/2927
See application file for complete search history.

(56) References Cited

U.S. PATENT DOCUMENTS

| | | | | |
|---|---|---|---|---|
| 5,301,539 A | * | 4/1994 | Schramm | C09K 8/594 73/53.01 |
| 5,465,610 A | * | 11/1995 | Loisel | G01N 13/00 356/440 |
| 5,597,950 A | * | 1/1997 | Mullen | G01F 23/241 73/53.01 |
| 5,824,886 A | * | 10/1998 | Selby | B01L 7/00 73/60.11 |
| 6,328,916 B1 | * | 12/2001 | Nishikawa | B29C 44/3446 264/50 |
| 6,640,618 B2 | * | 11/2003 | Kirts | G01N 13/02 250/357.1 |

\* cited by examiner

DEVICE FOR EVALUATING FOAMING PROPERTY OF GAS-SOLUBLE SURFACTANT AND APPLICATION THEREOF

This application is the U.S. national phase of International Application No. PCT/CN2015/078483 Filed on 7 May 2015 which designated the U.S. and claims priority to Chinese Application Nos. 201410212430.X filed on 19 May 2014, the entire contents of each of which are hereby incorporated by reference.

TECHNICAL FIELD

The present invention relates to a device for evaluating the foaming property of a gas-soluble surfactant and an application thereof and belongs to the technical field of researches on improving the exploitation efficiency of oil and gas field with carbon dioxide.

BACKGROUND ART

It has been a history of more than 50 years for the development of a technology for improving oil recovery rate through injection of carbon dioxide ($CO_2$), which has been widely applied worldwide as an important technology for improving the oil recovery rate. Among the total number of global EOR projects, gas drive projects account for 54%, i.e. among the global EOR projects, nearly half of the global EOR projects are gas drive projects; among all the gas drive projects, the number of $CO_2$ projects accounts for as much as nearly 77% alone; therefore, the technology for improving the oil recovery rate with $CO_2$ drive accounts for 41.46% of the total global EOR projects, which has become one of the most important techniques for improving the oil recovery rate.

However, in the on-site application of a carbon dioxide drive technology, the carbon dioxide will be subject to viscous fingering and gravitational differentiation in a displacement process due to its relatively low viscosity and density. The viscous fingering makes the injected carbon dioxide channel through bypassing replaced crude oil and reduces sweep efficiency, and when there are cracks in a stratum, it will be more serious. Therefore, the critical part for improving the gas injection effect is to control the fluidity of the carbon dioxide to slow down gas channeling.

At present, the common technologies for controlling the fluidity of the carbon dioxide can be a water gas alternating injection technology and a foam flooding technology. For the problems such as poor injectability of low permeability oil reservoir water and foam fluid and instability of conventional carbon dioxide foam, provided is a method for fully utilizing the characteristic that supercritical carbon dioxide is a good solvent, adopting the gas-soluble surfactant, and injecting it into the stratum by means of taking carbon dioxide as a carrier to carry the gas-soluble surfactant to produce supercritical carbon dioxide foam in order to control the carbon dioxide fluidity.

the supercritical carbon dioxide foam fluidity control technology based on the gas-soluble surfactant is still in an early stage of research and development, and the key to successfully apply this technology is to develop a high-efficiency low-cost carbon dioxide gas-soluble surfactant, wherein the high efficiency refers to: such surfactant first, has good solubility in the supercritical carbon dioxide, i.e., being capable of taking carbon dioxide as a carrier;

second, has good foaming ability, i.e., being capable of producing foam when meeting water and having good foaming volume and foam half-life; and finally, has good post-bursting foam regenerating property, i.e., after the foam bursts in a stratum, when carbon dioxide floats upwards under the action of gravitational differentiation, the gas-soluble surfactant can foam again under the carrying of the upward floating carbon dioxide.

Therefore, it needs to establish a set of device and method for actually and precisely evaluating the foaming property of the gas-soluble surfactant.

Terminology Description gas-soluble surfactant: such surfactant is described relative to water-soluble surfactants, the current research is mainly directed to nonionic surfactants such as branched and linear alkylphenol polyoxyethylene and branched alkyl polyoxyethylene ether having ethoxylated hydrophile, carbon dioxide-philic hydrocarbon groups or hydrocarbon oxide groups and the like, such surfactant is also water soluble, but can be dissolved in the carbon dioxide in small amounts when the carbon dioxide is in the supercritical condition, and it is called gas-soluble surfactant ($CO_2$ soluble surfactants) to be differentiated from a conventional water soluble surfactant.

SUMMARY OF THE INVENTION

With regard to the defect of the prior art, the present invention provides a device for evaluating the foaming property of a gas-soluble surfactant.

The present invention also relates to a method for evaluating the foaming property of the gas-soluble surfactant by use of the device. The device and method of the present invention are used to evaluate the ability of supercritical carbon dioxide to carry such gas-soluble surfactant, the foaming property of such gas-soluble surfactant as well as its regenerating property after foam bursting.

The technical scheme of the present invention is as follows:

a device for evaluating the foaming property of a gas-soluble surfactant comprises: a gas source part, an evaluating kettle, a liquid part, and an intermediate container part;

according to the present invention, preferably, the gas source part comprises a carbon dioxide gas source;

the evaluating kettle comprises a cylindrical kettle body, a first piston arranged inside the cylindrical kettle body, and a first set of valves and a second set of valves arranged at two axial ends of the cylindrical kettle body, respectively, and the first piston divides the cylindrical kettle body into a displacement chamber and a mixing chamber, wherein the displacement chamber is connected with a first constant-flux pump and a first liquid storage tank through the first set of valves, the mixing chamber is connected separately with a gas pipeline and a liquid pipeline through the second set of valves, the gas pipeline is connected with the carbon dioxide gas source, and the liquid pipeline is connected separately with the liquid part and the intermediate container part through a third set of valves; a first pressure sensor is arranged on the first set of valves; a third pressure sensor is arranged on the third set of valves; the first pressure sensor directly measures the pressure in the displacement chamber 17-1, and since the pressure of the displacement chamber 17-1 equals to that of the mixing chamber 17-2, the pressure measured by the first pressure sensor is also the pressure of the mixing chamber 17-2. The third pressure sensor 20 has the functions the same as a sensor 13, and is also used to directly measure the pressure of an evaluating chamber 23-1, thereby measuring the pressure of a pressure regulating chamber 23-2;

the liquid part comprises the liquid pipeline and a fourth set of valves connected in sequence, the fourth set of valves comprising three paths, wherein the first path is connected with a micro pump containing the gas-soluble surfactant, the second path is connected with a second liquid storage tank through a second constant-flux pump, and the third path is an emptying valve;

the intermediate container part comprises a cylindrical intermediate container and a second piston arranged in the cylindrical intermediate container, the second piston divides the cylindrical intermediate container into an evaluating chamber and a pressure regulating chamber, the third set of valves is connected with the evaluating chamber, the pressure regulating chamber is communicated with a third liquid storage tank through a fifth valve and a third constant-flux pump respectively, and the pressure regulating chamber is further communicated with a fourth liquid storage tank through a sixth valve and a back-pressure valve;

an observation window is arranged on the surface of the cylindrical kettle body; and a heating jacket is installed at the outside of the evaluating kettle.

According to the present invention, preferably, the carbon dioxide gas source comprises a liquid carbon dioxide source, a plunger pump and a flowmeter, wherein the liquid carbon dioxide source is connected with the gas pipeline through the plunger pump and the flowmeter in sequence. The flowmeter is used for metering an injection speed and an accumulated injection amount of liquid carbon dioxide.

According to the present invention, preferably, the liquid carbon dioxide source comprises a carbon dioxide gas cylinder, a dryer and a refrigeration part, which are connected in sequence, and the refrigeration part comprises a refrigerator, a coil pipe arranged in the refrigerator and a high pressure storage tank. The design herein has the advantages that the amount of carbon dioxide is convenient to meter, and the design herein has the beneficial effects that the experimental carbon dioxide is dried to prevent moisture contained in the carbon dioxide from icing to block the pipeline in a subsequent refrigeration process. The refrigerator 4 is used for liquefying the carbon dioxide and storing liquid carbon dioxide at a constant temperature, the coil pipe is arranged in the refrigerator for prolonging the flow time of the carbon dioxide in the refrigerator so as to fully liquefy the carbon dioxide, and the high pressure storage tank is used for storing the liquid carbon dioxide.

According to the present invention, preferably, a first base is installed at the bottom of the evaluating kettle, and the first base drives the cylindrical kettle body to rotate along a horizontal axial direction; and the pipelines respectively connected with the evaluating kettle are flexible pipelines.

In the device of the present invention, the first constant-flux pump is used for pumping distilled water contained in the first liquid storage tank into an upper space of the first piston 15 at a desired speed: the direct function of pumping the distilled water is to propel the first piston to move, so as to change the pressure in a mixing chamber, but when the second set of valves is controlled to connect the mixing chamber with the evaluating chamber, when acting on the first piston, the pumped distilled water propels the first piston and drives fluid in the mixing chamber to flow into the evaluating chamber at a certain speed, so that the distilled water is pumped to play the two functions; and a lower space of the first piston, namely the mixing chamber is used for evaluating the solubility of the gas-soluble surfactant in the supercritical carbon dioxide, the forming ability of the gas-soluble surfactant and the regenerating ability of foam generated by the gas-soluble surfactant after bursting.

The first base is used for supporting the evaluating kettle, and a power unit is installed on a bracket part to ensure rotation of the evaluating kettle; the micro pump is used for quantitatively injecting gas-soluble surfactant into the evaluating kettle; the third pressure sensor is used for monitoring the pressure of the mixing chamber in the evaluating kettle and the pressure of the intermediate container; the third pressure sensor is connected to the second set of valves, and is respectively connected to the evaluating chamber and the fourth set of valves through the third set of valves, therefore, when the set of valves, connected to the third pressure sensor, of the second set of valves is opened, the third pressure sensor measures the pressure of the lower space of the first piston in the evaluating kettle, if the set of valves, connected to the fourth set of valves, of the third set of valves is opened at this moment, then the micro pump or the second constant-flux pump is connected to the third pressure sensor, thus the pressure of the micro pump or the pressure of the second constant-flux pump are measured at the same time; if the set of valves connected to the evaluating chamber of the third set of valves is opened, then the third pressure sensor is connected to the evaluating chamber, thus the pressure of the evaluating chamber is measured.

The inside of the intermediate container is provided with a second piston, used for storing the fluid in the evaluating kettle under the condition that the pressure of the evaluating kettle is kept unchanged, wherein the purpose of storing the fluid in the evaluating kettle is as follows: when the foaming ability of gas-soluble surfactant is evaluated, it is necessary to firstly prepare supercritical carbon dioxide gas in which a certain gas-soluble surfactant is dissolved in the mixing chamber, then to transfer the prepared supercritical carbon dioxide gas in the mixing chamber to the evaluating chamber of the intermediate container to be stored, with the pressure kept unchanged, (the reason that the pressure is kept unchanged during the transfer is that the change of pressure may result in precipitation of the gas-soluble surfactant, thereby changing the solubility of the gas-soluble surfactant in evaluation of the forming ability.) finally to store the prepared supercritical carbon dioxide gas in the evaluating chamber of the intermediate container before cleaning the mixing chamber, to inject distilled water into it with the constant-flux pump, and to pump the supercritical carbon dioxide from the evaluating chamber of the intermediate container into the mixing chamber 17-2 for a foaming ability test.

The second base is used for fixing the intermediate container; the second constant-flux pump is used for pumping the distilled water in the second liquid storage tank into the evaluating kettle, the distilled water is pumped into the mixing chamber 17-2 via the second set of valves 18 when the valve 26-2 and the third set of valves 21 are started at the same time, the second constant-flux pump plays a role in the foaming ability test; and the micro pump is used for pumping the gas-soluble surfactant into the mixing chamber 17-2 via the second set of valves 18 when the valve 26-3 and the third set of valves 21 are started at the same time, and plays a role in adding the gas-soluble surfactant in the mixing chamber 17-2 when testing the solubility of the gas-soluble surfactant in the supercritical carbon dioxide and preparing supercritical carbon dioxide gas in which a certain amount of gas-soluble surfactant is dissolved these two processes are performed at the same time, thus the distilled water and the micro pump are pumped in respectively for evaluation of the foaming ability of the gas-soluble surfactant and regenerating ability after foam bursting; the emptying valve is used for emptying and cleaning the internal liquid of the evaluating valve; the third constant-flux pump 30 is used for pumping the distilled water in the third liquid storage tank 31 into the intermediate container 23, which plays a role of pumping the distilled water into the lower space of the second piston of the intermediate container 23 via the third constant-flux pump 30 to regulate pressure of the upper space, namely the evaluating chamber 23-1 of the piston of the intermediate container 23; the back-pressure valve 32 is used for controlling the internal fluid pressure of the intermediate container 23 to ensure that the pressure of the intermediate container 23 is the set pressure during movement of the second piston 22; the fourth liquid storage tank 33 is used for storing the liquid discharged from the intermediate container 23; the fourth liquid storage tank 33 is communicated with the lower space, namely pressure regulating chamber 23-2 of the intermediate container 23 via the back-pressure valve 32 and the sixth valve 24-2, therefore, when the second piston 22 in the intermediate container 23 moves downwards and compresses the distilled water in the pressure regulating chamber 23-2 to allow its pressure to rise to the starting pressure of the back-pressure valve 32, the distilled water in the pressure regulating chamber 23-2 will flow into the fourth liquid storage tank 33, and therefore, the fourth liquid storage tank 33 is used for storing the distilled water discharged from the interior of the pressure regulating chamber 23-2 during pressure regulation.

a method for evaluating foaming property of a gas-soluble surfactant by use of the device, comprising the following steps:

(I) measuring the solubility of various gas-soluble surfactants in supercritical $CO_2$ at different pressures or temperatures;

(1) metering the addition amount of carbon dioxide in the evaluating kettle by use of the flowmeter;

(2) injecting the gas-soluble surfactant into the evaluating kettle by use of a micro pump;

(4) closing a second set of valves, heating the evaluating kettle to a set analog bottom layer temperature, keeping the temperature unchanged, and recording the pressure in the evaluating kettle through a first pressure sensor when the temperature is stable;

(5) driving the evaluating kettle to rotate for 1-2 hours along the horizontal axial direction at a constant speed by use of the first base, and recording the pressure in the evaluating kettle;

(6) observing whether the system in the evaluating kettle is turbid through a visual window, adjusting the pressure of the evaluating kettle by use of a first constant-flux pump and a first set of valves to change the turbidity of the system in the evaluating kettle or not, and recording the pressure and temperature when the turbid solution in the evaluating kettle is changed from being turbid into clear; the specific operation is: pumping the distilled water into the evaluating kettle by the first constant-flux pump to increase the pressure in the evaluating kettle, and discharging the liquid by starting the first set of valves to lower the pressure in the evaluating kettle;

(7) by means of a ratio of the mass of the gas-soluble surfactant pumped into the evaluating kettle to the mass of the carbon dioxide pumped into the evaluating kettle recorded in the entire test process, calculating according to a formula I to obtain the solubility of the gas-soluble surfactant in the supercritical carbon dioxide under the pressure and temperature conditions recorded in the step (6):

the solubility of the gas-soluble surfactant in the supercritical carbon dioxide=the mass of the gas-soluble surfactant/the mass of the carbon dioxide*100%     (1)

Figure 2:
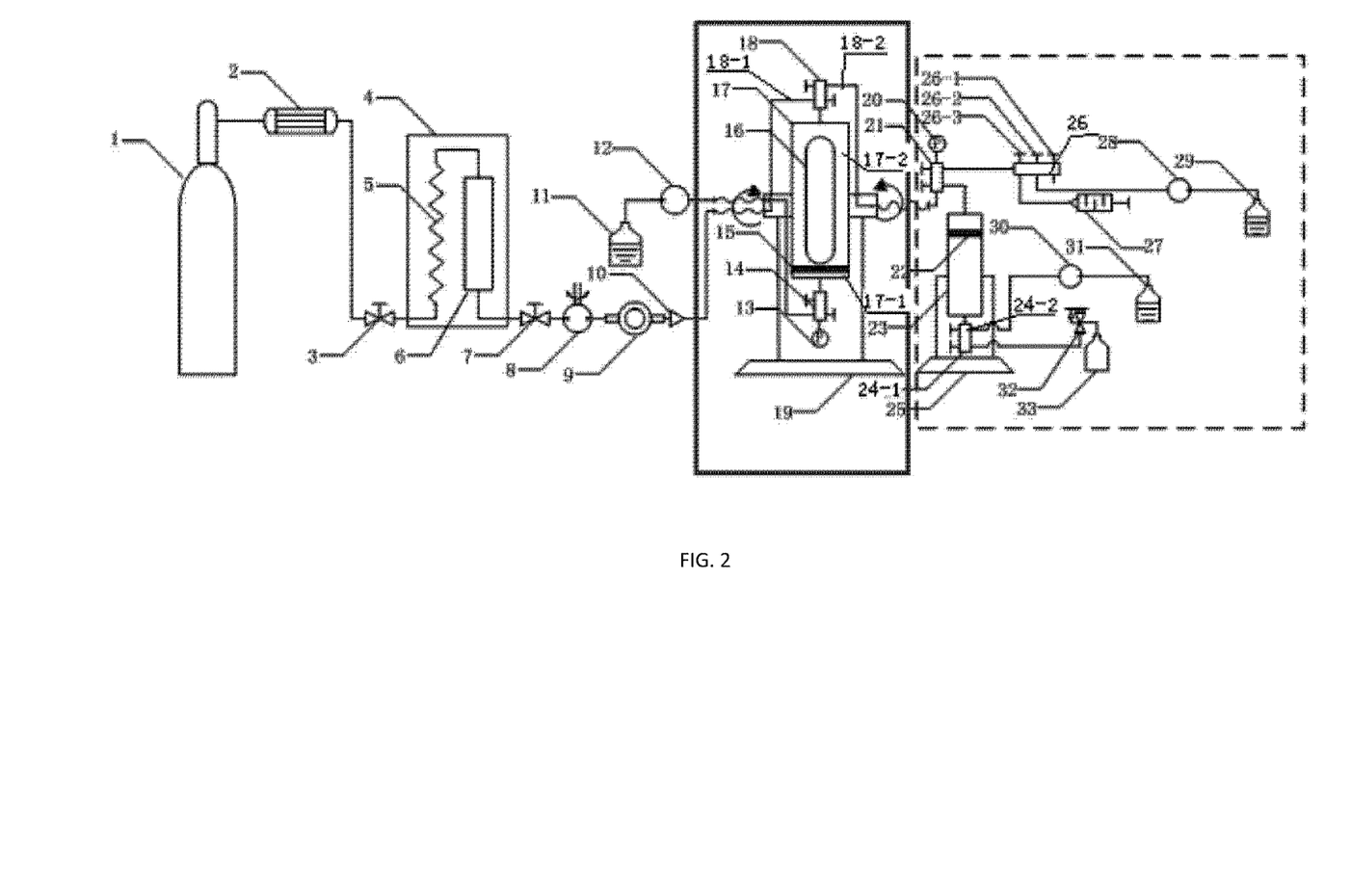
FIG. 2 shows a device for evaluating the foaming property of the gas-soluble surfactant after the evaluating kettle 17 turns for 180 degrees.

(II) Evaluating the foaming ability of the gas-soluble surfactant (1) preparing the supercritical carbon dioxide in which a certain amount of gas-soluble surfactant is dissolved in the evaluating kettle using the method in the step (I);

(2) pumping distilled water into an intermediate container through a fifth valve by using a third constant-flux pump to adjust the internal pressure of the intermediate container to be consistent with the pressure of the evaluating kettle, monitoring the pressure in the intermediate container through a third pressure sensor, and closing the fifth valve after the pressure is stable;

(3) setting the opening pressure of a back-pressure valve as follows: 0.1 MPa higher than the pressure in the evaluating kettle;

(4) opening the third constant-flux pump, setting the third constant-flux pump as a constant pressure injection mode, setting the pressure of the third constant-flux pump to be consistent with the pressure in the evaluating kettle, then opening valves extending to a liquid pipeline in the second set of valves, a third set of valves and a sixth valve, and pumping all the supercritical carbon dioxide in which the gas-soluble surfactant is dissolved from the evaluating kettle into the intermediate container on the condition of keeping the pressure and temperature conditions unchanged;

(5) closing the third set of valves, cleaning the interior of the evaluating kettle by using a second constant-flux pump and an emptying valve, and locating a first piston at a topmost position, wherein the internal pressure of the evaluating kettle is the barometric pressure;

(6) pumping a certain amount of distilled water into the evaluating kettle by using the second constant-flux pump;

(7) pumping the supercritical carbon dioxide in which the gas-soluble surfactant is dissolved, stored in the intermediate container into the evaluating kettle, monitoring the first pressure sensor and the foaming column height, and recording the foaming half life;

(III) Evaluating the post-bursting foam regenerating ability after the foaming of the gas-soluble surfactant (1) after the foam produced in the evaluating kettle in the step (II) bursts, rotating the evaluating kettle by 180 degrees in a horizontal axial direction, as shown by the red solid line frame in FIG. 2;

(2) pumping the supercritical carbon dioxide gas at the upper layer of the evaluating kettle after the foam bursts into an intermediate container under the condition of a constant pressure and temperature in accordance with the method of pumping the supercritical carbon dioxide gas in which the gas-soluble surfactant is dissolved in the evaluating kettle into the intermediate container under the condition of a constant pressure and temperature in the step (II);

the process is only for pumping the supercritical carbon dioxide into the intermediate container, the objective of this step is that the supercritical carbon dioxide is at the upper part of the container after the foam bursts because of the fact that its density is smaller than that of water, and the supercritical carbon dioxide in the upper space carries part of the gas-soluble surfactant because of the fact that it can dissolve a certain amount of gas-soluble surfactant, origin of the so-called "part of" lies in after foaming, part of the gas-soluble surfactant remains in the lower part of the distilled water after the foam bursts. The distilled water remaining in the evaluating kettle 17 needs to be discharged, because the water-soluble surfactant dissolved in water will be remained inside it, thus affecting the follow-up evaluation on the regenerating ability after foam bursting. The evaluation on the regenerating ability after the foam bursting refers to: there is foam again when the supercritical carbon dioxide gas meets the distilled water during floating upwards for the reason that it can dissolve a certain amount of gas-soluble surfactant under the effect of gravitational differentiation when it is floating upwards, therefore, the remained distilled water needs to be discharged and then replaced with new distilled water for testing in order to precisely test its foaming ability;

(3) the foaming ability evaluation test is performed in accordance with the steps (6), (7) in the step (II) to simulate a process in which foam occurs again when the supercritical carbon dioxide gas carrying the gas-soluble surfactant meets the water during floating upwards under the effect of the gravitational differentiation to evaluate its regenerating ability after the foam bursts.

preferably, in accordance with the present invention, the pumping process of the carbon dioxide in the step (1) of the step (I) is:

(1.1) drying carbon dioxide in a carbon dioxide gas cylinder through a dryer, then feeding the carbon dioxide into a coil pipe, refrigerating the carbon dioxide into liquid carbon dioxide through a refrigerator and then storing the liquid carbon dioxide in a high pressure storage tank;

(1.2) pumping the liquid carbon dioxide stored in the high pressure storage tank into an evaluating kettle through a plunger pump, and controlling the pumping speed and amount of the liquid carbon dioxide with a flowmeter.

the present invention has the following advantages and significant effects:

1. the device is internally provided with a refrigerating unit, namely the refrigerator 4 so that carbon dioxide can be injected in a liquid way during the test. In addition, the injection amount of the carbon dioxide can be measured conveniently, test accuracy is improved, and the liquid carbon dioxide injection way in the test is consistent with the liquid carbon dioxide injection way adopted at an oil field site;

2. the evaluating kettle 17 in the device of the present invention is provided with a temperature and pressure resistant visible glass window 16, thus ensuring that a cloud point method can be used when testing the solubility of the gas-soluble surfactant in the supercritical carbon dioxide, and the foam form and foam performance can be observed in the foaming ability evaluation process of the gas-soluble surfactant;

3. the evaluating kettle 17 in the device of the present invention is internally provided with a piston 15, so that in the test process, the pressure of the evaluating kettle 17 can be maintained or raised in a manner of pumping distilled water into the evaluating kettle 17 by using a constant-flux pump 12, and the pressure of the evaluating kettle 17 can be reduced in a manner of discharging the distilled water out by opening the valve 14-2, and therefore, the control on the pressure of the evaluating kettle 17 is realized, and the cloud point pressure and the cloud point temperature of the gas-soluble surfactant in the supercritical carbon dioxide can be conveniently measured.

Figure 1:
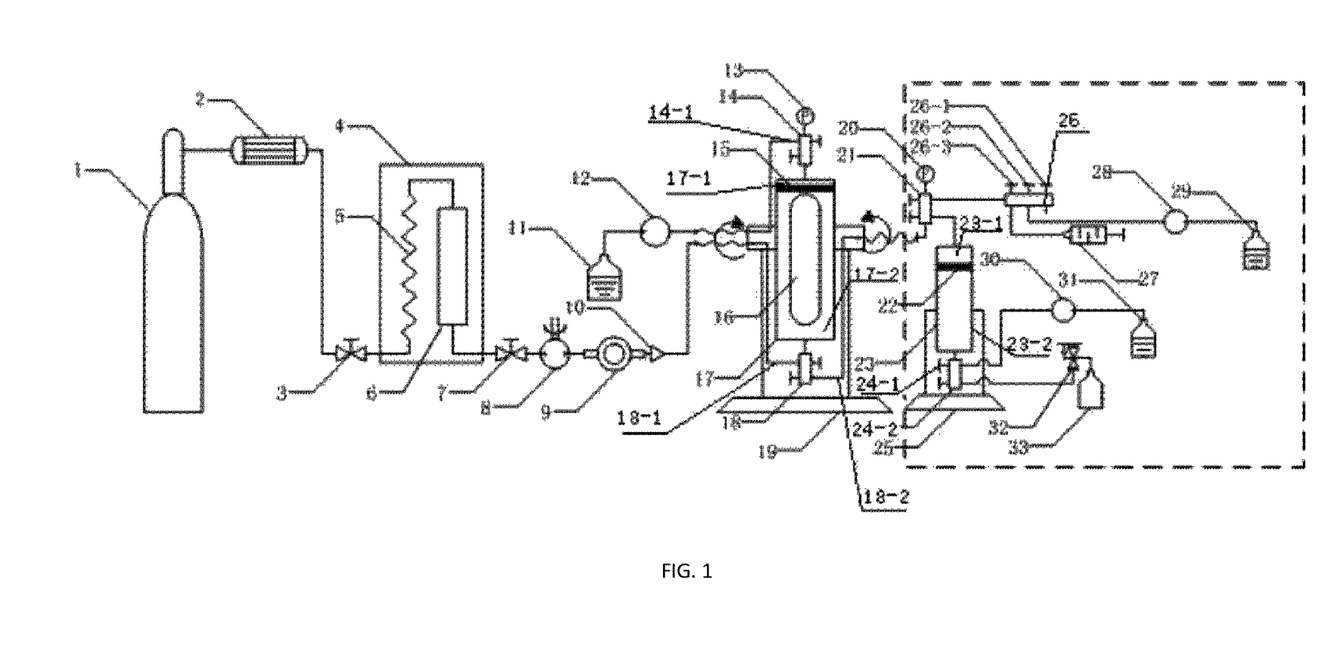
FIG. 1 shows a device for evaluating the foaming property of the gas-soluble surfactant.

4. the device of the present invention is internally provided with a fluid storage unit under pressure and temperature. Main working parts of the fluid storage unit under pressure and temperature include: an intermediate container 23, a constant-flux pump 30 and a back-pressure valve 32. When provided with the fluid storage unit under pressure and temperature, the followings can be achieved:

① the supercritical carbon dioxide in which the gas-soluble surfactants is completely dissolved, prepared in the evaluating kettle can be transferred into the intermediate container under the condition of constant pressure and temperature, and therefore, precipitation of the gas-soluble surfactant, test errors and test accuracy reduction caused by adverse effect, caused by the changes of the pressure or temperature, on the solubility of the gas-soluble surfactant in the supercritical carbon dioxide can be avoided by the implementation of the function;

② when the evaluating kettle 17 rotates to the position shown in FIG. 2, supercritical carbon dioxide gas which floats upwards under the effect of gravitational differentiation in the evaluating kettle 17 after foam bursts can be transferred into the intermediate container 23 under the condition of constant pressure and temperature, so that the next test on the regenerating ability after foam bursting can be carried out;

5. a power device is arranged on a base 19 of the device of the present invention, so that the evaluating kettle 17 can turn at 360 degrees in the direction shown in FIG. 1, further the gas-soluble surfactant and the supercritical carbon dioxide can be sufficiently and evenly mixed when measuring the solubility of the gas-soluble surfactant in the supercritical carbon dioxide, and a phase equilibrium state can be realized; and in the process of measuring the regenerating property of the gas-soluble surfactant after foam bursting, the floating upwards of the supercritical carbon dioxide under the effect of gravitational differentiation after foam bursting can be simulated by moving the evaluating kettle 17 to the position shown in FIG. 2, and further the foam regenerating property of the gas-soluble surfactant can be evaluated.

BRIEF DESCRIPTION OF THE DRAWINGS

wherein: 1—carbon dioxide gas cylinder; 2—dryer; 3—valve; 4—refrigerator; 5—coil pipe; 6—high pressure storage tank; 7—valve; 8—plunger pump; 9—flowmeter; 10—check valve; 11—first liquid storage tank; 12—first constant-flux pump; 13—first pressure sensor; 14—first set of valves; 14-1—a path in the first set of valves 14; 15—first piston; 16—observation window; 17—evaluating kettle; 17-1—displacement chamber; 17-2—mixing chamber; 18—second set of valves; 18-1—gas pipeline; 18-2—liquid pipeline; 19—first base; 20—third pressure sensor; 21—third set of valves; 22—second piston; 23—intermediate container; 23-1—evaluating chamber; 23-2—pressure regulating chamber; 24—fourth set of valves; 24-1—fifth valve; 24-2—sixth valve; 25—second base; 26—fourth set of valves; 26-1—emptying valve in the fourth set of valves 26; 26-2—second path in the fourth set of valves 26; 26-3—first path in the fourth set of valves 26; 27—micro pump; 28—second constant-flux pump; 29—second liquid storage tank; 30—third constant-flux pump; 31—third liquid storage tank; 32—back-pressure valve; 33—fourth liquid storage tank.

DETAILED DESCRIPTION OF THE INVENTION

Principles, specific structures and the most preferable embodiments of the present invention will now be described with reference to the accompanying drawings and should not be construed as being limitative thereof.

Embodiment 1

A device for evaluating the foaming property of a gas-soluble surfactant, which comprises a gas source part, an evaluating kettle, a liquid part, and an intermediate container part;

the gas source part comprises a carbon dioxide gas source;

the evaluating kettle 17 comprises a cylindrical kettle body, a first piston 15 arranged inside the cylindrical kettle body, and a first set of valves 14 and a second set of valves 18 respectively arranged at two axial ends of the cylindrical kettle body, the first piston 15 divides the cylindrical kettle body into a displacement chamber 17-1 and a mixing chamber 17-2, wherein the displacement chamber 17-1 is connected with a first constant-flux pump 14 and a first liquid storage tank 11 through the first set of valves 12, the mixing chamber 17-2 is respectively connected with a gas pipeline 18-1 and a liquid pipeline 18-2 through the second set of valves 18, the gas pipeline 18-1 is connected with the carbon dioxide gas source, and the liquid pipeline 18-2 is connected with the liquid part and the intermediate container part through the third set of valves 21; the first pressure sensor 13 is arranged on the first set of valves 14; the third pressure sensor 20 is arranged on the third set of valves 21;

the liquid part comprises the liquid pipeline and a fourth set of valves 26 connected in sequence, the fourth set of valves 26 comprises three paths, wherein the first path 26-3 is connected with a micro pump 27 filled with the gas-soluble surfactant, the second path 26-2 is connected with a second liquid storage tank through a second constant-flux pump, and the third path is an emptying valve 26-1;

the intermediate container part comprises a cylindrical intermediate container 23 and a second piston 22 arranged in the cylindrical intermediate container 23, the second piston 22 divides the cylindrical intermediate container 23 into an evaluating chamber 23-1 and a pressure regulating chamber 23-2, the third set of valves 21 is connected with the evaluating chamber 17, the pressure regulating chamber 23-2 is communicated with a third liquid storage tank 31 through a fifth valve 24-1 and a third constant-flux pump 30 respectively, and the pressure regulating chamber 23-2 is further communicated with a fourth liquid storage tank 33 through a sixth valve 24-2 and a back-pressure valve 32;

an observation window 16 is arranged on the surface of the cylindrical kettle body; a heating jacket is installed at the outside of the evaluating kettle.

the carbon dioxide gas source comprises a liquid carbon dioxide source, a plunger pump 8 and a flowmeter 9, wherein the liquid carbon dioxide source is connected with the gas pipeline 18-1 through the plunger pump 8 and the flowmeter 9 in sequence. The flowmeter is used for metering an injection speed and an accumulated injection amount of liquid carbon dioxide.

Embodiment 2

According to a device for evaluating the foaming property of a gas-soluble surfactant of the embodiment 1, the differences lie in that the liquid carbon dioxide source comprises a carbon dioxide gas cylinder 1, a dryer 2 and a refrigeration part, which are connected in sequence, and the refrigeration part comprises a refrigerator 4, a coil pipe 5 arranged in the refrigerator 4 and a high pressure storage tank 6.

Embodiment 3

According to a device for evaluating the foaming property of a gas-soluble surfactant of the embodiment 1, the differences lie that a first base 19 is installed at the bottom of the evaluating kettle 17, and the first base 19 drives the cylindrical kettle body to rotate along a horizontal axial direction; the pipelines respectively connected with the evaluating kettle 17 are flexible pipelines.

Embodiment 4

A method for evaluating foaming property of a gas-soluble surfactant by use of the device in embodiments 1-3, comprising the following steps:

(I) measuring the solubility of various gas-soluble surfactants in supercritical $CO_2$ at different pressures or temperatures;

(1) metering the addition amount of carbon dioxide in the evaluating kettle 17 by using the flowmeter 9;

(2) injecting the gas-soluble surfactant into the evaluating kettle 17 by using a micro pump 27;

(4) closing a second set of valves 18, heating the evaluating kettle 17 to a set analog bottom layer temperature, keeping the temperature unchanged, and recording the pressure in the evaluating kettle 17 through a first pressure sensor 13 when the temperature is stable;

(5) driving the evaluating kettle 17 to rotate for 1-2 hours along the horizontal axial direction at a constant speed by using the first base 19, and recording the pressure in the evaluating kettle 17;

(6) observing whether the system in the evaluating kettle 17 is turbid through a visual window 16, adjusting the pressure of the evaluating kettle 17 by using a first constant-flux pump 12 and a first set of valves 14 to change the turbidity of the system in the evaluating kettle 17 or not, and recording the pressure and temperature when the turbid solution in the evaluating kettle 17 is changed from being turbid into clear; the specific operation is: pumping the distilled water into the evaluating kettle 17 by the first constant-flux pump 12 to increase the pressure in the evaluating kettle 17, and discharging the liquid by starting the first set of valves 14 to lower the pressure in the evaluating kettle 17;

(7) by means of a ratio of the mass of the gas-soluble surfactant pumped into the evaluating kettle 17 to the mass of the carbon dioxide pumped into the evaluating kettle 17 recorded in the entire test process, calculating according to a formula I to obtain the solubility of the gas-soluble surfactant in the supercritical carbon dioxide under the pressure and temperature conditions recorded in the step (6):

the solubility of the gas-soluble surfactant in the supercritical carbon dioxide=the mass of the gas-soluble surfactant/the mass of the carbon dioxide*100%   (1)

(II) Evaluating the foaming ability of the gas-soluble surfactant (1) preparing the supercritical carbon dioxide in which a certain amount of gas-soluble surfactant is dissolved in the evaluating kettle 17 by using the method in the step (I);

(2) pumping distilled water into an intermediate container 23 through a fifth valve 24-1 by using a third constant-flux pump 30 to adjust the internal pressure of the intermediate container 23 to be consistent with the pressure of the evaluating kettle 17, monitoring the pressure in the intermediate container 23 through a third pressure sensor 20, and closing the fifth valve 24-1 after the pressure is stable;

(3) setting the opening pressure of a back-pressure valve 32 as follows: 0.1 MPa higher than the pressure in the evaluating kettle 17;

(4) opening the third constant-flux pump 30, setting the third constant-flux pump 30 as a constant pressure injection mode, setting the pressure of the third constant-flux pump to be consistent with the pressure in the evaluating kettle 17, then opening valves extending to a liquid pipeline 18-2 in the second set of valves 18, a third set of valves 21 and a sixth valve 24-2, and pumping all the supercritical carbon dioxide in which the gas-soluble surfactant is dissolved in the evaluating kettle 17 into the intermediate container 23 under the condition of constant pressure and temperature;

(5) closing the third set of valves 21, cleaning the interior of the evaluating kettle 17 by using a second constant-flux pump 28 and an emptying valve 26-1, and locating a first piston 15 at a topmost end, wherein the internal pressure of the evaluating kettle 17 is the barometric pressure;

(6) pumping a certain amount of distilled water into the evaluating kettle 17 by using the second constant-flux pump 28;

(7) pumping the supercritical carbon dioxide in which the gas-soluble surfactant is dissolved, stored in the intermediate container 23 into the evaluating kettle 17, monitoring the first pressure sensor 13 and the foaming column height, and recording the foaming half life;

(III) Evaluating the post-bursting foam regenerating ability after the foaming of the gas-soluble surfactant (1) after the foam produced in the evaluating kettle in the step (II), rotating the evaluating kettle by 180 degrees in a horizontal axial direction, as shown by the red solid line frame in FIG. 2;

(2) pumping the supercritical carbon dioxide gas at the upper layer of the evaluating kettle after the foam bursts into an intermediate container 23 under the condition of a constant pressure and temperature in accordance with a method of pumping the supercritical carbon dioxide gas in which the gas-soluble surfactant is dissolved from the evaluating kettle into the intermediate container under the condition of a constant pressure and temperature in the step (II); the process is only for pumping the supercritical carbon dioxide into the intermediate container 23, the objective of this step is that the supercritical carbon dioxide is at the upper part of the container after foaming bursting because of the fact that its density is smaller than that of water, the supercritical carbon dioxide in the upper space carries part of the gas-soluble surfactant because of the fact that it can dissolve a certain amount of gas-soluble surfactant, origin of the so-called "part of" lies in after foaming, part of the gas-soluble surfactant remains in the lower part of the distilled water after the foam bursting. The distilled water remaining in the evaluating kettle 17 needs to be discharged, because the water-soluble surfactant dissolved in water will be remained inside it, thus affecting the follow-up evaluation on the regenerating ability after the foam bursting. The evaluation on the regenerating ability after the foam bursting refers to: there is foam again when the supercritical carbon dioxide gas meets the distilled water during floating upwards for the reason that it can dissolve a certain amount of gas-soluble surfactant under the effect of gravitational differentiation when it is floating upwards, therefore, the remained distilled water needs to be discharged and then replaced with new distilled water for testing in order to precisely test its foaming ability;

(3) the foaming ability evaluation test is performed in accordance with the steps (6), (7) in the step (II) to simulate a process in which foam occurs again when the supercritical carbon dioxide gas carrying the gas-soluble surfactant meets the water during floating upwards under the effect of gravitational differentiation to evaluate its regenerating ability after the foam bursts.

Embodiment 5

According to the method for evaluating foaming property of the gas-soluble surfactant in embodiment 4, the differences lie in that the pumping process for the carbon dioxide in the step (1) of the step (I) is:

(1.1) drying carbon dioxide in a carbon dioxide gas cylinder through a dryer 2, then feeding the carbon dioxide into a coil pipe 5, refrigerating the carbon dioxide into liquid carbon dioxide through a refrigerator 4 and then storing the liquid carbon dioxide in a high pressure storage tank 6;

(1.2) pumping liquid carbon dioxide stored in the high pressure storage tank 6 into an evaluating kettle 17 through a plunger pump 8, and controlling the pumping speed and amount of the liquid carbon dioxide with a flowmeter 9.

What is claimed is:
1. A device for evaluating the foaming property of a gas-soluble surfactant, characterized in that the device comprises a gas source part, an evaluating kettle, a liquid part, and an intermediate container part;

the gas source part comprises a carbon dioxide gas source;
the evaluating kettle comprises a cylindrical kettle body, a first piston arranged inside the cylindrical kettle body, and a first set of valves and a second set of valves respectively arranged at two axial ends of the cylindrical kettle body, the first piston divides the cylindrical kettle body into a displacement chamber and a mixing chamber, wherein the displacement chamber is connected with a first constant-flux pump and a first liquid storage tank through the first set of valves, the mixing chamber is respectively connected with a gas pipeline and a liquid pipeline through the second set of valves, the gas pipeline is connected with the carbon dioxide gas source, and the liquid pipeline is respectively connected with the liquid part and the intermediate container part through a third set of valves; a first pressure sensor is arranged on the first set of valves; a third pressure sensor is arranged on the third set of valves;

the liquid part comprises the liquid pipeline and a fourth set of valves connected in sequence, the fourth set of valves comprises three paths, wherein the first path is connected with a micro pump filled with the gas-soluble surfactant, the second path is connected with a second liquid storage tank through a second constant-flux pump, and the third path is an emptying valve;

the intermediate container part comprises a cylindrical intermediate container and a second piston arranged inside the cylindrical intermediate container, the second piston divides the cylindrical intermediate container into an evaluating chamber and a pressure regulating chamber, the third set of valves is connected with the evaluating chamber, the pressure regulating chamber is in communication with a third liquid storage tank respectively through a fifth valve and a third constant-flux pump, and the pressure regulating chamber is further in communication with a fourth liquid storage tank through a sixth valve and a back-pressure valve; an observation window is arranged on the surface of the cylindrical kettle body; and a heating jacket is mounted outside the evaluating kettle.

2. The device for evaluating the foaming property of the gas-soluble surfactant according to claim 1, characterized in that the carbon dioxide gas source comprises a liquid carbon dioxide source, a plunger pump and a flowmeter, wherein the liquid carbon dioxide source is connected with the gas pipeline through the plunger pump and the flowmeter in sequence.

3. The device for evaluating the foaming property of the gas-soluble surfactant according to claim 2, characterized in that the liquid carbon dioxide source comprises a carbon dioxide gas cylinder, a dryer and a refrigeration part which is connected in sequence, wherein the refrigeration part comprises a refrigerator, a coil pipe arranged in the refrigerator and a high pressure storage tank.

4. The device for evaluating the foaming property of the gas-soluble surfactant according to claim 1, characterized in that a first base is installed at bottom of the evaluating kettle, and the first base drives the cylindrical kettle body to rotate along a horizontal axial direction; and all the pipelines respectively connected with the evaluating kettle are flexible pipelines.

5. A method for evaluating the foaming property of a gas-soluble surfactant by use of the device of claim 1, comprising the following steps:
   (I) measuring the solubility of various gas-soluble surfactants in supercritical $CO_2$ at different pressures or temperatures;
   (1) determining the additional amount of carbon dioxide in the evaluating kettle by use of a flowmeter;
   (2) injecting the gas-soluble surfactant into the evaluating kettle by use of the micro pump;
   (4) closing the second set of valves, heating the evaluating kettle to a set analog bottom layer temperature, keeping the temperature constant, and recording the pressure in the evaluating kettle through the first pressure sensor when the temperature is stable;
   (5) driving the evaluating kettle to rotate for 1-2 hours along the horizontal axial direction at a constant speed by use of the first base, and recording the pressure in the evaluating kettle;
   (6) observing whether the system in the evaluating kettle is turbid through a visual window, adjusting the pressure of the evaluating kettle by use of the first constant-flux pump and the first set of valves to change turbidity of the system in the evaluating kettle or not, and recording the pressure and temperature when turbid solution in the evaluating kettle is changed from turbid into clear;
   (7) by means of a ratio of mass of the gas-soluble surfactant pumped into the evaluating kettle to the mass of the carbon dioxide pumped into the evaluating kettle recorded in the entire test process, calculating according to a formula I to obtain the solubility of the gas-soluble surfactant in supercritical carbon dioxide under the pressure and temperature conditions recorded in the step (6):

$$\text{the solubility of the gas-soluble surfactant in the supercritical carbon dioxide} = \frac{\text{the mass of the gas-soluble surfactant}}{\text{the mass of the carbon dioxide}} * 100\% \quad \text{(I)}$$

(II) evaluating foaming property of the gas-soluble surfactant;
   (1) preparing supercritical carbon dioxide in which a certain amount of gas-soluble surfactant is dissolved in the evaluating kettle by use of the method in the step (1);
   (2) pumping distilled water into the intermediate container through the fifth valve by use of the third constant-flux pump to adjust the internal pressure of the intermediate container to be consistent with the pressure of the evaluating kettle, monitoring the pressure in the intermediate container through the third pressure sensor, and closing the fifth valve after the pressure is stable;
   (3) setting opening pressure of the back-pressure valve as follows: 0.1 MPa higher than the pressure in the evaluating kettle;
   (4) opening the third constant-flux pump, setting the third constant-flux pump as a constant pressure injection mode, setting the pressure of the third constant-flux pump to be consistent with the pressure in the evaluating kettle, then opening valves extending to a liquid pipeline in the second set of valves, the third set of valves and the sixth valve, and pumping all supercritical carbon dioxide in which the gas-soluble surfactant is dissolved from the evaluating kettle into the intermediate container under the condition of constant pressure and temperature;
   (5) closing the third set of valves, cleaning the interior of the evaluating kettle by use of the second constant-flux pump and the emptying valve, and locating the first piston at a topmost position, wherein the internal pressure of the evaluating kettle is the barometric pressure;
   (6) pumping a certain amount of distilled water into the evaluating kettle by use of the second constant-flux pump;
   (7) pumping supercritical carbon dioxide in which the gas-soluble surfactant is dissolved, stored in the intermediate container into the evaluating kettle, monitoring the first pressure sensor and foaming column height, and recording a foam half-life;
   (III) evaluating post-bursting foam regenerating ability after the foaming of the gas-soluble surfactant;
   (1) after the foam produced in the evaluating kettle in the step (II) bursts, rotating the evaluating kettle by 180 degrees in a horizontal axial direction;
   (2) pumping supercritical carbon dioxide gas at mid-upper layer of the evaluating kettle after foam bursting, into the intermediate container under the condition of constant pressure and temperature, in accordance with the method of pumping supercritical carbon dioxide gas in which the gas-soluble surfactant is dissolved, from the evaluating kettle into the intermediate container under the condition of constant pressure and temperature in the step (II);
   (3) performing a foaming ability evaluation test in accordance with the steps (6) and (7) in the step (II) to simulate a process in which after the foam in the step (II) bursts, foam occurs again when supercritical carbon dioxide gas carrying the gas-soluble surfactant meets water during floating upwards under gravitational differentiation, thereby evaluating post-bursting foam regenerating ability of the gas-soluble surfactant.

6. The method according to claim 5, characterized in that pumping process of the carbon dioxide in the step (1) of step (I) is:

(1.1) drying the carbon dioxide in the carbon dioxide gas cylinder through the dryer, then feeding the carbon dioxide into the coil pipe, refrigerating the carbon dioxide into liquid carbon dioxide through refrigerator and then storing the liquid carbon dioxide in a high pressure storage tank;

(1.2) pumping the liquid carbon dioxide stored in the high pressure storage tank into the evaluating kettle through the plunger pump, and controlling the pumping speed and amount of the liquid carbon dioxide with a flowmeter.

\* \* \* \* \*